US005798348A

United States Patent [19]

Alemany

[11] Patent Number: 5,798,348
[45] Date of Patent: Aug. 25, 1998

[54] FATTY-ACID MONOESTERS OF ESTROGENS FOR THE TREATMENT OF OBESITY AND/OR OVERWEIGHT

[75] Inventor: Maria Alemany, Barcelona, Spain

[73] Assignee: Laboratorios S.A.L.V.A.T., S.A., Esplugues de Llobregat, Spain

[21] Appl. No.: 739,165

[22] Filed: Oct. 30, 1996

[30] Foreign Application Priority Data

Oct. 30, 1995 [ES] Spain .................... 9502101

[51] Int. Cl.$^6$ .................... A61K 31/56; C07J 1/00; C07C 69/00
[52] U.S. Cl. .................... 514/182; 514/178; 552/617; 552/625; 560/138
[58] Field of Search .................... 514/178, 182, 514/549; 552/617, 625; 560/138

[56] References Cited

PUBLICATIONS

Zhang, Positional Cloning . . . . Dec. 1994, p. 425.
Vazquez–Alcantara, Long–Acting, Estrogenic . . . , J. steroid, 1989.
Clear, M. The Antiobesity Effect . . . , Hormel Institute, 1991
D. Sanchis, et al, Oleoyl–estrone . . . , Int. Journal of Obesity, 1996.

Primary Examiner—Raymond Henley, III
Attorney, Agent, or Firm—Michael J. Striker

[57] ABSTRACT

The pharmaceutical and/or cosmetic compositions for treatment of obesity and/or overweight contain an effective amount of a fatty-acid monoester of an estrogen and a fatty acid wherein the estrogen is estrone, diethylstilbestrol, estriol, estradiol or ethinyl estradiol and the fatty acid is oleic, linoleic, linolenic, stearic, palmitic, palmitoleic or arachidonic acids. The fatty-acid monoesters mimic the function of estrone monooleate, as a signal that informs the brain of the size of fat tissue mass. In preferred pharmaceutical and/or cosmetic compositions for intravenous injection the monoester is incorporated in a lipidic suspension, prepared from lipoproteins or from liposome components, such as soy oil and egg phospholipids. When administered to rats with a 15% of total adipose tissue, they produce weight reduction of about 10%, by a new and unexpected mechanism. They are useful for the treatment of obesity and/or overweight in mammals, with the advantages of high efficacy and low toxicity. New substantially pure fatty-acid monoesters including estrone monooleate and diethylstilbestrol monooleate are also described.

20 Claims, 2 Drawing Sheets

FATTY-ACID MONOESTERS OF ESTROGENS FOR THE TREATMENT OF OBESITY AND/OR OVERWEIGHT

BACKGROUND OF THE INVENTION

This invention refers to products, compositions and uses thereof, for therapeutic and/or cosmetic treatment of obesity and/or overweight in mammals.

Treatment of obesity and/or overweight is a therapeutic or cosmetic problem of major importance that does not have a satisfactory solution yet. Attempts to solve the problem by reducing food intake or by doing physical exercise, are well known. But also known are the difficulties, limitations and general lack of success of all these approaches. Apparently the sheer complexity of mechanisms involved in the control of body mass allow little room for external manipulation, thus limiting the possible damage to body reserves by increased thermogenic stimulation or diminished energy intake.

In the therapeutic fight against obesity and/or overweight considerable research has been focused on trying to find some signal that informs the brain of the size of fat tissue mass. It is believed that such information is required by the brain to promote either the accumulation of fat reserves or their burning by the thermogenic system, via the natural homeostatic mechanisms set to maintain the body mass stable. According to a recent discovery based on a mutation of a gene, one such signal could be a protein named leptin (cf. Y. Zhang et al., Nature 1994, vol. 372, pp. 425–32). From this discovery the invention of using leptin for the preparation of a medicament for treating obesity by injection could be derived. But, even if this approach proves to be useful in the future, it would be very expensive because leptin must be prepared by genetic engineering.

Estradiol or estra-1,3,5(10)-triene-3,17-diol is a natural estrogen widely used in estrogenic hormone therapy. Estradiol monoesters at C-17 and C-3 with palmitic, stearic, and oleic acids have been chemically synthesized and their long-term estrogenic responses in ovariectomized rats have been reported (cf. M. A. Vazquez-Alcantara et al., *J. Steroid Biochem.* 1989, vol. 33, pp. 1111–8). But nothing about their use in the treatment of obesity has been suggested.

The steroid dehydroepiandrosterone (DHEA) at high doses has been found to slim rats without apparent adverse side-effects (cf. M. P. Cleary, *Proc.Soc.ExR.Biol.Med.* 1991, vol.196, pp. 8–16). However, at the lower doses usable in humans, all attempts to use DHEA as anti-obesity agent have failed.

Thus, the provision of satisfactory new products for the treatment of obesity and/or overweight is still an unresolved problem.

SUMMARY OF THE INVENTION

In this specification the term "estrogens" refers to the substances tending to promote estrus and stimulate the development of female secondary sex characteristics. This term comprises natural, semisynthetic and synthetic estrogens, both steroidal and nonsteroidal, such as estrone, diethylstilbestrol, estriol, estradiol and ethinyl estradiol. In this specification the term "fatty acids" refers to the carboxylic acids which are components of natural fats, such as oleic, linoleic, linolenic, stearic, palmitic, palmitoleic, and arachidonic acids.

The present invention proposes a new solution to the above-mentioned problem, by providing substantially pure new fatty-acid monoesters of estrogens and fatty acids, wherein:

a) the estrogen is selected from the group consisting of estrone, i.e. 3-hydroxyestra-1,3,5(10)-trien-17-one; diethylstilbestrol, i.e. 4,4'-(1,2-diethyl-1,2-ethenediyl)-bisphenol; estriol, i.e. estra-1,3,5(10)triene-3,16,17-triol, and ethinylestradiol, i.e. 19-nor-17a-pregna-1,3,5(10)-trien-20-yne-3,17-diol;

b) the fatty acid is selected from the group consisting of oleic, linoleic, linolenic, stearic, palmitic, palmitoleic and arachidonic acids; and c) with the proviso that, when the estrogen is steroidal, the acyl group is attached to the hydroxyl group at the C-3 position of the steroid ring system.

In a preferred embodiment the fatty-acid is oleic acid. In a more preferred embodiment the estrogen is selected from the group consisting of estrone and diethylstilbestrol.

A particularly preferred product of this invention is estrone monooleate or [3(Z)]-3-[(1-oxo-9-octadecenyl)oxy]-estra-1,3,5(10)-trien-17-one of formula I:

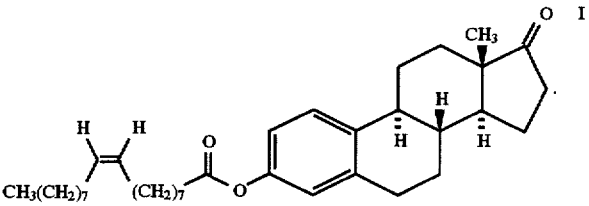

Another particularly preferred product of this invention is diethylstilbestrol monooleate or [4(Z)]-4-[(1-oxo-9-octadecenyl)-oxy]-4,4'-(1,2-diethyl-1,2-ethenediyl)bisphenol, of formula II:

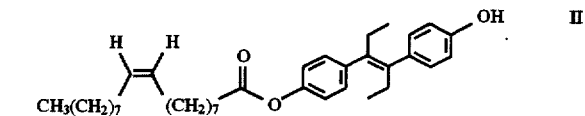

As illustrated in the accompanying examples, the new products of this invention can be prepared by reaction between the corresponding estrogen and some activated forms of the corresponding fatty acid (e.g. the acid chloride), in an appropriate solvent (e.g. pyridine), followed by appropriate separation and purification (e.g. by column or HPLC chromatography).

This invention is partially a consequence of the unexpected finding, made by the inventors, that estrone monooleate (I) is a chemically new product involved in the control of body weight in mammals. Estrone monooleate and a postulated lipophilic pathway for its transport by lipoproteins, is being disclosed for the first time in a journal article published by the inventors themselves after this invention was made (cf. "Oleoyl-estrone induces the loss of body fat in rats", *Int. J. Obes.* 1996, vol.20, pp. 588–94). After the publication of this article, Chemical Abstracts Service (CAS) has recorded estrone monooleate (I) for the first time, with CAS Registry Number [180003-17-2].

Estrone monooleate behaves as a distinct hormone, different from estrone. Apparently, the fatty-acid monoesters of estrogens which are the subject matter of this invention, are products that mimic the hormone activity of estrone monooleate, as a signal that informs the brain of the size of fat tissue mass.

Another aspect of this invention relates to the provision of pharmaceutical and/or cosmetic compositions comprising a therapeutically and/or cosmetically effective amount of the above-mentioned fatty-acid monoesters of estrogens, and appropriate amounts of excipients suitable for the desired administration via.

In principle, the compositions of this invention can be administered by standard delivery systems: oral, anal, vaginal, topical, transdermal or parenteral (intravenous, intramuscular or subcutaneous). However, not all the administration vias are equally effective. A preferred one is the intravenous injection of a formulation where the fatty-acid monoester of the estrogen is integrated in a lipidic suspension. In a particular embodiment this lipidic suspension is a lipoprotein suspension. In another embodiment the lipidic suspension is a liposome suspension, preferably obtained by addition of soy oil and egg phospholipids.

A preferred delivery system for the compositions of this invention is the continuous intravenous injection of the fatty-acid monoester integrated in a lipidic suspension. The formulation should be substantially isotonic with the blood of the treated mammal, and it should contain the monoester in the form of a stable lipidic suspension, i.e., in the form of finally divided particles incorporated in suspended microdrops with protecting layers of lipids, these lipids being of lipoproteins or of any common constituents of liposomes.

A typical preparation of the above-mentioned preferred formulation comprises the steps of: a) mixing a lipidic solution of a fatty-acid monoester of an estrogen with an isotonic aqueous phase; and b) sonicating the obtained mixture until a stable suspension is reached. Common techniques of liposome preparations can be used for this preparation. The formulation can be commercially distributed either ready-for-use or in a concentrated form. It can also be distributed with the monoester and the lipids separated, as a kit-of-parts.

Another aspect of this invention relates to the use of a fatty-acid monoester of an estrogen for the preparation of a medicament or formulation for the treatment of obesity and/or overweight in mammals. This use is related to a method of treatment of a mammal suffering from obesity, and/or of a person willing to reduce weight for cosmetic reasons, comprising the administration of a therapeutically and/or cosmetically effective amount of a fatty-acid monoester of an estrogen, together with appropriate amounts of excipients suitable for the desired administration via. In all these cases: a) the estrogen is selected from the group consisting of estrone, diethyl-stilbestrol, estriol, estradiol and ethinyl estradiol; b) the fatty acid is selected from the group consisting of oleic, linoleic, linolenic, stearic, palmitic, palmitoleic and arachidonic acids; and c) with the proviso that the acyl group is attached to the hydroxyl group at the C-3 position of the steroid ring system when the estrogen is steroidal. It is noteworthy that the use (or method of treatment) of the C-3 fatty-acid monoesters of estradiol in the field of obesity/weight reduction is part of this invention. This is so because no disclosure or suggestion of this new use has been given, although the products per se were chemically described (see background art).

BRIEF DESCRIPTION OF THE DRAWING

The objects, features and advantages of the invention will now be illustrated in more detail with the aid of the following description of the preferred embodiments, with reference to the accompanying figures in which.

DESCRIPTION OF THE PREFERRED EMBODIMENTS

Figure 1:
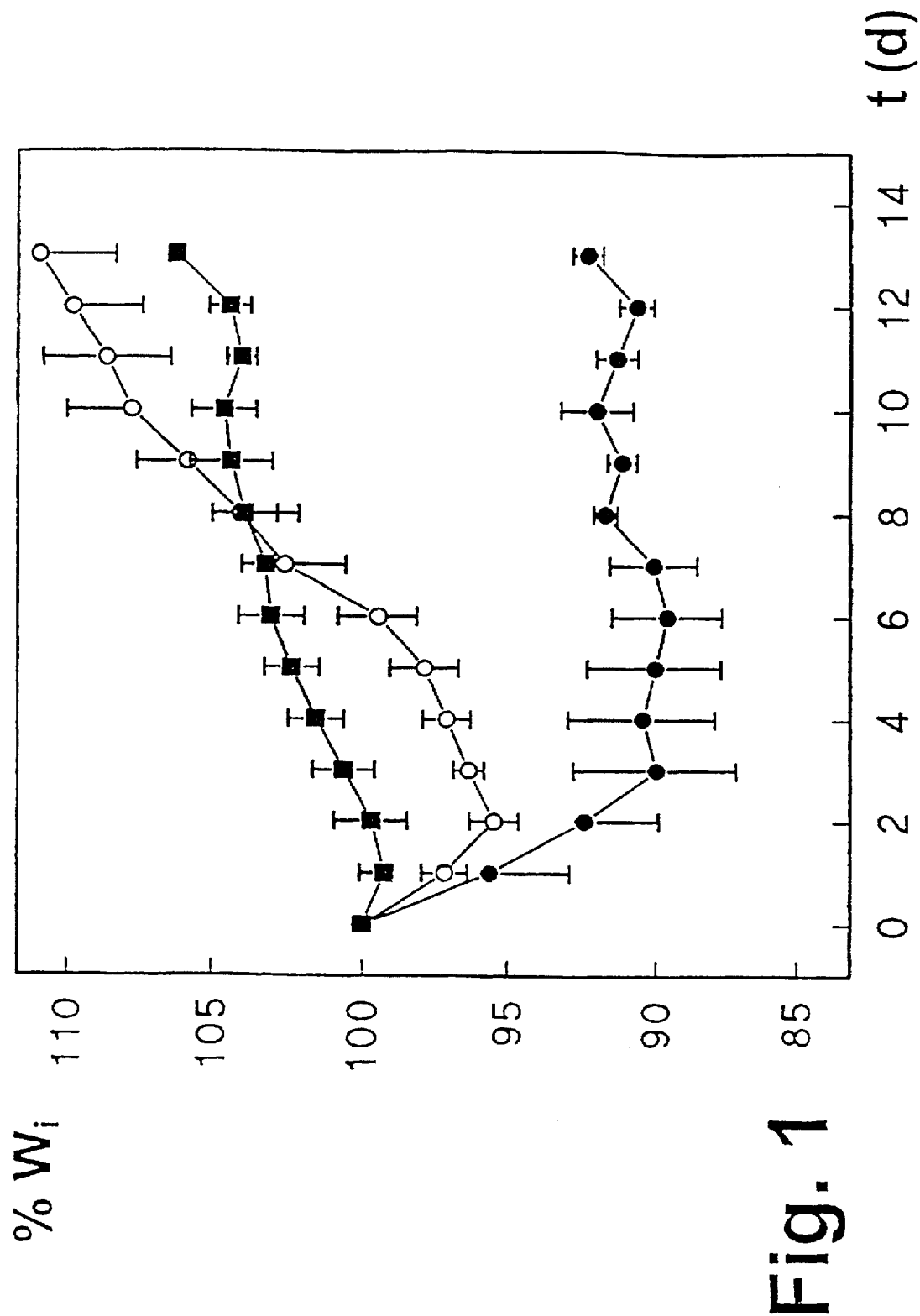
FIG. 1 is a graphical illustration of the change in body weight of female rats during estrone and estrone monooleate treatments; W (%) represents body weight expressed as percentage of the initial body weight (100%) and t(d) represents time of treatment expressed in days; filled squares represent controls; empty circles represent treatment with estrone and filled circles represent treatment with estrone monooleate; the W (%) values are the mean ± SEM of 4–5 different rats per group; during the treatments estrone and estrone monooleate were given at the same dose: 3.1 nmol per day and per gram of body weight and the controls received the same liposomes but without hormone.
Figure 2:
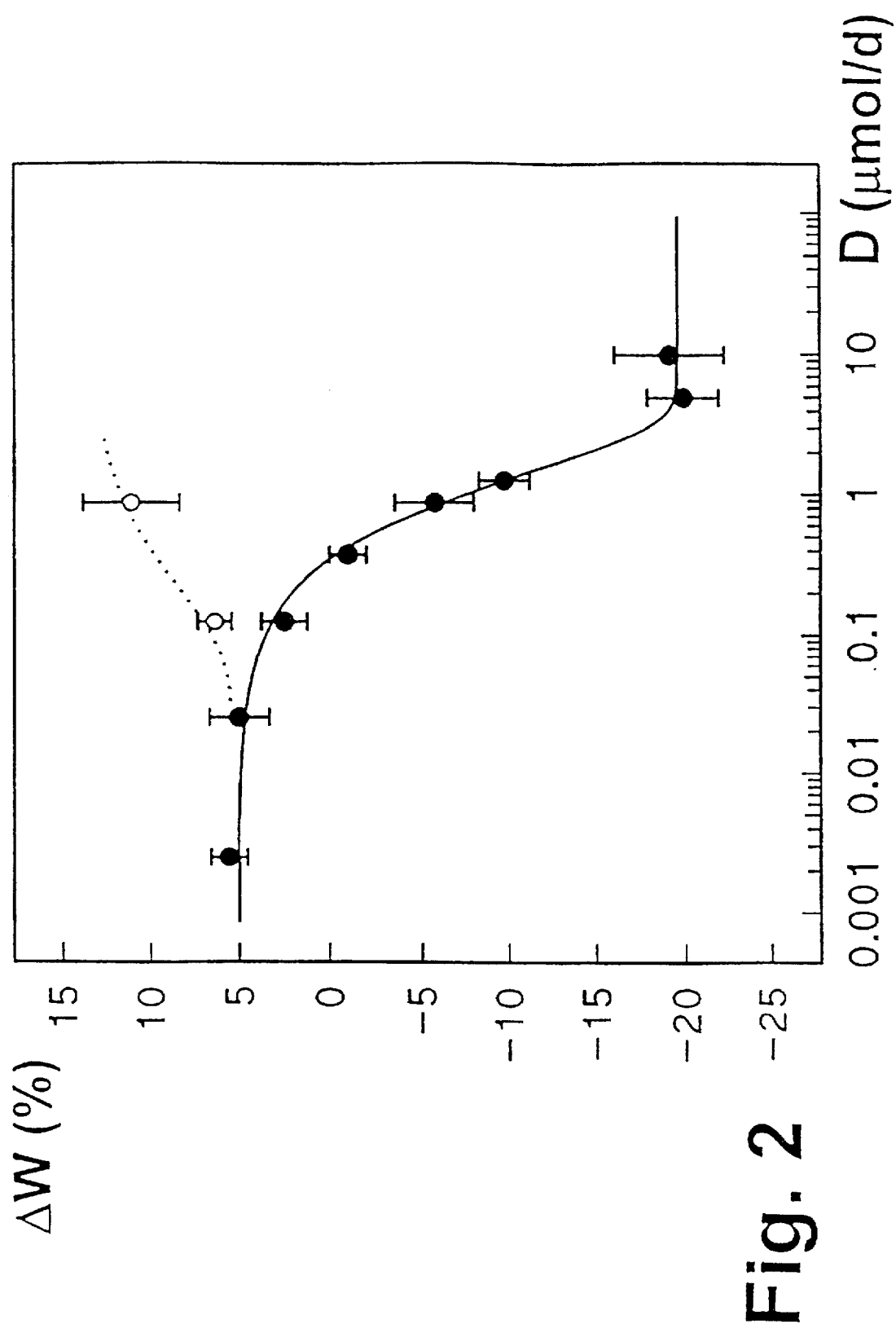
FIG. 2 is a graphical illustration of the overall effect on body weight of treatments of female rats with different doses of estrone monooleate (filled circles) for a period of 14 days and in which the empty circles depict the effect of estrone administration. $\Delta W(\%)$ represents the weight change expressed as a percentage of initial weight (0%); D($\mu$mol/d) represents the administered dose, expressed as micromoles per day; and each circle is the mean ± SEM of 4–5 different animals and corresponds to the change in body mass observed only at the end of a 2-week period. The administration of estrone had no overall effect on body weight. During the same period, control rats gained about 5% in body weight. The rats studied had about 15% of adipose tissue.

In the accompanying examples some experimental results illustrate the invention. The pharmacological results come from experiments with rats, as animal models of human beings. Example 1 illustrates the detection of estrone monooleate in the rat white adipose tissue. Example 2 illustrates the preparation of estrone monooleate, both normal and labeled, from commercially available chemicals and radiochemicals. Example 3 illustrates the preparation of a liposome from a lipid emulsion of soy oil and egg phospholipids in isotonic water, of a type commonly used in hospitals for parenteral nutrition. Example 4 and FIG. 1 illustrate the weight reduction caused by intravenous administration of estrone monooleate in rats. Having in mind that the rats studied had about 15% of adipose tissue, the weight reduction associated with this invention can be qualified as surprisingly high. Example 5 and FIG. 2 illustrate that the weight reduction is dependent on the dose of the monoester, and that a relatively small dose is already effective. They also illustrate that the effect of the fatty-acid monoester of the estrogen cannot be attributed to the liberation of the estrogen itself. Example 6 illustrates the preparation of diethyl-stilbestrol monooleate. Example 7 illustrates intravenous, oral and subcutaneous administrations of diethylstilbestrol monooleate.

The results presented in the accompanying examples hint strongly of the existence of a lipophilic hormone pathway between tissues, in which the hydrophobic hormones are incorporated into lipoproteins, which travel by the bloodstream to be anchored in target tissues with specific receptors for their apoproteins (or by lipoprotein lipase). In the target tissue, the estrogen monoester is rapidly released and most of it is immediately split by esterases. The rapid disappearance of estrone monooleate label from the blood and its immediate destruction in most tissues give weight to the role of estrone monooleate as a "hot" molecule with short life and deep physiological effect, both essential traits of regular hormones. This is in open contradiction with the very long-term estrogenic action of depot injections of other estrogen esters used for deep and lasting estrogenization, the key for the difference being precisely in the incorporation into the postulated lipophilic pathway. Therefore, all the previous art concerning the therapeutic administration of estrogens has no relation to the present invention.

The physiological actions induced by chronic treatment of rats with estrone monooleate are quite different from those induced by estrone (cf. FIGS. 1 and 2). Thus, the loss of weight induced by the fatty-acid monoesters of estrogen of this invention is not directly attributable to the liberation of the estrogen moiety by an esterase.

Other physiological effects induced by chronic treatment of rats with estrone monooleate are quite different from those induced by estrogens. At the doses administered there was no significant swelling of the uterus (weight in the control group, 0.98±0.12 g; in estrone monooleate treated with 0.78 μmol/day, 1.27±0.29 g; difference is not significant), which also indicates that the effects on body weight are not a consequence of deep estrogenization, but rather attributable to the whole monoester.

From these findings it is clear that the therapeutic or cosmetic treatment of obesity and/or overweight that derives from this invention is novel and unexpected, and that it represents a real breakthrough in this technical field, having advantages over the treatments previously proposed in the art.

Among these advantages, efficiency is surely the most evident one. Nevertheless, safety (lack of toxicity) is important as well. The accompanying examples further illustrate the invention.

EXAMPLE 1: Detection of Estrone Monooleate in Rat Adipose Tissue

Tissue samples of Wistar rats were extracted with trichloromethane; then the hydrophilic materials were extracted from the organic phase with water. Most of triacylglycerols were later eliminated using a column of silica gel, and the remaining polar components were removed with a column of neutral alumina. Steroid monoesters share in the final extract increased tenfold with respect to the fresh tissue. This fraction was analyzed on a Kontron (Milan, Italy) HPLC furnished with a K440 diode-array detector and LB5074 radioactivity detector (Berthold, Regensdorf Switzerland) on line. The presence of estrone monooleate was confirmed by matching the position, spectrum and coincidence of peaks, by using internal standards of labeled monoester, prepared according to Example 2. A number of other peaks presented the typical spectrum of aromatized steroids, which evidences that there are several molecular species of estrogen in white adipose tissue. The contents of estrone monooleate in visceral fat samples from female rats was 15–45 μmol/kg.

EXAMPLE 2: Preparation of Estrone Monooleate, and of a Labeled Sample Thereof 200 mg of estrone were mixed with 2 mL of chilled anhydrous pyridine and 400 mg of oleoyl chloride. The mixture was maintained at 40° C. for 12 h. Estrone monooleate was purified by extracting excess pyridine and estrone monooleate with HCl, and then neutralizing with NaHCO$_3$. The monoester was further purified by passing it through a silica gel column using a mobile phase of hexane/diethylether/acetic acid (20:5:1 by volume). The estrone monooleate fractions were pooled and dried under vacuum. A substantially pure oil was obtained, with the following spectroscopic data: IR (film), cm$^{-1}$:3050–3020, 2990–2850, 1750, 1730, 1610, 1580, 1500; $^1$H-NMR (CDCl$_3$, 200 MHz), ppm: 7.20–6.80 (8H, complex, aromatic), 5.40–5.30 (2H, CH—CH), 5.00 (OH), 2.20–2.15 (4H, CH$_2$—CO), 2.10–2.00 (2H, CH$_2$—COO); and MS (electroimpact, 70 eV): 534 (M+).

Trace amounts of high specific activity labeled estrone monooleate were prepared using the same procedure and tritium-labeled estrone (NEN, N.J. USA). The monoester was separated from the free hormone by thin layer chromatography on activated silica gel plates, using hexane/ethyl ether/acetic acid (20:10:1) as eluent. This same setting was later used to determine the integrity of the monoester molecule in tissue extracts.

EXAMPLE 3: Incorporation of Estrone Monooleate into Liposomes and its Administration to Rats Estrone monooleate was incorporated into liposomes by dissolving the monoester in the lipid (200 g soy oil and 12 g egg phospholipids per liter of isotonic solution), then incorporating the aqueous phase and finally sonicating the mixture; the mean droplet diameter was lower than 1 μm. This stable preparation, containing 20% lipid, was administered to rats for 14-day periods using Alzet osmotic minipumps (model 2ML2; Alza, Los Angeles, Calif., USA), which injected its contents at a rate of 5 μl/h. The minipumps were inserted subcutaneously in the back under ether anesthesia, and were connected via a short capillary tube to the left jugular vein.

EXAMPLE 4: Weight Reduction Caused by Intravenous Administration of Estrone Monooleate in Rats The chronic injection of estrone monooleate at rates as low as 0.25 μmol per day induced a steady loss of weight. FIG. 1 shows the effect of the administration of 0.78 μmoles per day on Wistar rats (weighing initially 245–255 g), compared with controls and with rats receiving the same dose of free estrone. After a rapid loss of weight in the first days of treatment, counter-regulatory mechanisms diminished the rate of weight loss and, at low doses, induced a trend to recover the initial body weight. Another factor which may explain the marked tapering off of body weight records under estrone monooleate treatment was the limit set by the amount of fat reserves in the rats studied: about 15% of their body weight. The energy and hydric balances of the animals studied was consistent with a loss of fat tissue and not with a simple loss of fluids.

EXAMPLE 5: Dependence of Weight Reduction on Dose of Estrone Monooleate.

The effects on body mass after 14 days of estrone monooleate treatment are presented in FIG. 2. The loss of weight was dependent on the dose administered within the range of 0.2–2 μmol/day. The effects of chronic administration of estrone on body mass, even at high doses, were much less marked in deepness and duration, with no effects on body mass after 14 days. The effects observed were not directly traceable to the liberation of the estrogen moiety, since the effects of estrone on body mass were (significantly) less marked than doses of estrone monooleate ten times lower. In addition, no estrogenic effects were observed in rats under estrone monooleate treatment. The rats lost weight with no other apparent effects apart from a partially diminished food intake.

EXAMPLE 6: Preparation of Diethylstilbestreate

In a flask under nitrogen atmosphere, with reflux condenser and magnetic stirring, 5 g (18.6 mmol) of diethylstilbestrol and 66 mL of anhydrous pyridine were placed. The mixture was cooled in an ice bath, and 5.6 g (18.6 mmol) of oleoyl chloride were added dropwise. The mixture was kept at room temperature for 17 h, with constant stirring. Then 5 L of dichloromethane were added, and the solution was washed three times with 2 L of 1M HCl aqueous solution, three times with 5% sodium hydrogen carbonate aqueous solution, and finally two times with 2 L of water. The organic layer was dried with anhydrous sodium sulfate. Solvent evaporation under reduced pressure yielded 9.85 g of a reddish oil. After purification by flash column chromatography (700 g silica as support, dichloromethane as eluent), 5.0 g of the title compound were obtained, as a slightly yellow oil, with a purity above 90%, and the following spectroscopic data: IR (film), cm$^{-1}$: 3500–3000, 1750, 1730, 1600f 1500, 1200, 833, 758; $^1$H-NMR (CDCl$_3$, 200 MHz), ppm: 7.20–6.80 (8H, complex, aromatic), 5.40–5.30 (2H, CH=CH), 5.00 (OH), 2.30–2.20 (4H, diethyl-stilbestrol CH$_2$), 2.10–2.00 (4H, complex, CH$_2$-COO and CH$_2$-C=C), 1.80–0.60 (complex, other CH$_2$ and CH$_3$); and MS (electroimpact, 70 eV): 532 (M+).

EXAMPLE 7: Intravenous, Subcutaneous and Oral Administration of Diethylstilbestrol Monooleate to Rats In an experiment of intravenous administration, analogous to the one of Example 4 (10 rats, 3.5 µmol/day for 14 days) but with diethylstilbestrol monooleate instead of estrone monooleate, a 10% reduction in body weight was obtained at a 30% higher speed.

A comparative experiment of subcutaneous administration of diethylstilbestrol monooleate induced a body weight reduction similar to the intravenous administration of the same dose of this product, at a slightly slower speed.

A comparative experiment of oral administration of diethylstilbestrol monooleate (5 µmol dissolved in oil, with a gastric tube and once per day), also induced a weight reduction of 8–10%, with about 30% slower speed.

What is claimed is:

1. A substantially pure fatty-acid monoester of an estrogen and a fatty acid, said fatty acid including an acyl group; wherein the estrogen is selected from the group consisting of estrone, diethylstilbestrol, estriol and ethinyl estradiol; the fatty acid is selected from the group consisting of oleic, linoleic, linolenic, stearic, palmitic, palmitoleic and arachidonic acids; and with the proviso that, when the estrogen is steroidal and has a steroid ring system with a C-3 position and a hydroxyl group at the C-3 position, the acyl group of the fatty acid is attached to the hydroxyl group at the C-3 position of the steroid ring system in the fatty acid monoester.

2. The fatty-acid monoester according to claim 1, wherein the fatty acid is said oleic acid.

3. A substantially pure fatty-acid monoester selected from the group consisting of consisting of estrone monooleate and diethylstilbestrol monooleate.

4. A substantially pure fatty-acid monoester consisting of estrone monooleate.

5. A substantially pure fatty-acid monoester consisting of diethylstilbestrol monooleate.

6. A substantially pure fatty-acid monoester of an estrogen and a fatty acid, said fatty acid including an acyl group; wherein the estrogen is selected from the group consisting of diethylstilbestrol and ethinyl estradiol; the fatty acid is selected from the group consisting of oleic, linoleic, linolenic, stearic, palmitic, palmitoleic and arachidonic acids; and with the proviso that, when the estrogen is steroidal and has a steroid ring system with a C-3 position and a hydroxyl group at the C-3 position, the acyl group of the fatty acid is attached to the hydroxyl group at the C-3 position of the steroid ring system in the fatty acid monoester.

7. A pharmaceutical and/or cosmetic composition comprising a therapeutically and/or cosmetically effective amount of a substantially pure fatty-acid monoester of an estrogen and a fatty acid, said fatty acid including an acyl group, in combination with at least one excipient acceptable for a predetermined administration via and in an amount sufficient for the purposes thereof; wherein the estrogen is selected from the group consisting of estrone, diethylstilbestrol, estriol, estradiol and ethinyl estradiol; the fatty acid is selected from the group consisting of oleic, linoleic, linolenic, stearic, palmitic, palmitoleic and arachidonic acids; and with the proviso that, when the estrogen is steroidal and has a steroid ring system with a C-3 position and a hydroxyl group at the C-3 position, the acyl group of the fatty acid is attached to the hydroxyl group at the C-3 position of the steroid ring system in the fatty acid monoester.

8. The pharmaceutical and/or cosmetic composition according to claim 7, wherein said administration via is intravenous injection, and the fatty-acid monoester is entegrated in a lipidic suspension.

9. The pharmaceutical and/or cosmetic composition according to claim 7, wherein said lipidic suspension is a lipoprotein suspension.

10. The pharmaceutical and/or cosmetic composition according to claim 7, wherein said lipidic suspension is a liposome suspension.

11. The pharmaceutical and/or cosmetic composition according to claim 10, wherein said liposome suspension is obtainable by addition of soy oil and egg phospholipids.

12. A pharmaceutical and/or cosmetic composition comprising a therapeutically and/or cosmetically effective amount of a substantially pure fatty-acid monoester in combination with at least one excipient acceptable for a predetermined administration via and in an amount sufficient for the purposes thereof: wherein the fatty-acid monoester is selected from the group consisting of estrone monooleate and diethylstilbestrol monooleate.

13. A pharmaceutical and/or cosmetic composition comprising a therapeutically and/or cosmetically effective amount of a substantially pure fatty-acid monoester of diethylstilbestrol monooleate, in combination with at least one excipient acceptable for a predetermined administration via and in an amount sufficient for the purposes thereof.

14. A pharmaceutical and/or cosmetic composition comprising a therapeutically and/or cosmetically effective amount of a substantially pure fatty-acid monoester of an estrogen and a fatty acid, said fatty acid including an acyl group, in combination with at least one excipient acceptable for a predetermined administration via and in an amount sufficient for the purposes thereof; wherein the estrogen is selected from the group consisting of diethylstilbestrol and ethinyl estradiol; the fatty acid is selected from the group consisting of oleic, linoleic, linolenic, stearic, palmitic, palmitoleic and arachidonic acids; and with the proviso that, when the estrogen is steroidal and has a steroid ring system with a C-3 position and a hydroxyl group at the C-3 position, the acyl group of the fatty acid is attached to the hydroxyl group at the C-3 position of the steroid ring system in the fatty acid monoester.

15. A method of lowering body weight in a mammal comprising administering to said mammal an effective amount of a substantially pure fatty-acid monoester of an estrogen and a fatty acid, said fatty acid including an acyl group; wherein the estrogen is selected from the group consisting of estrone, diethylstilbestrol, estriol, estradiol and ethinyl estradiol, the fatty acid is selected from the group consisting of oleic, linoleic, linolenic, stearic, palmitic, palmitoleic and arachidonic acids, and with the proviso that, when the estrogen is steroidal and has a steroid ring system with a C-3 position and a hydroxyl group at the C-3 position, the acyl group of the fatty acid is attached to the hydroxyl group at the C-3 position of the steroid ring system to form the fatty acid monoester; in combination with amounts of at least one member selected from the group consisting of pharmaceutically acceptable excipients and cosmetically acceptable excipients in an amount sufficient for the purposes thereof.

16. The method according to claim 15, wherein the fatty-acid monoester is an estrogen monooleate.

17. The method according to claim 15, wherein the fatty-acid monoester is selected from the group consisting of estrone monooleate and diethylstilbestrol monooleate.

18. A method of lowering body weight in a mammal comprising administering to said mammal an effective amount of estrone monooleate in combination with amounts of at least one member selected from the group consisting of pharmaceutically acceptable excipients and cosmetically acceptable excipients in an amount sufficient for the purposes thereof.

19. A method of lowering body weight in a mammal comprising administering to said mammal an effective amount of diethylstilbestrol monooleate in combination with amounts of at least one member selected from the group consisting of pharmaceutically acceptable excipients and cosmetically acceptable excipients in an amount sufficient for the purposes thereof.

20. A method of lowering body weight in a mammal comprising administering to said mammal an effective amount of a substantially pure fatty-acid monoester of an estrogen and a fatty acid, said fatty acid including an acyl group; wherein the estrogen is selected from the group consisting of diethylstilbestrol and ethinyl estradiol, the fatty acid is selected from the group consisting of oleic, linoleic, linolenic, stearic, palmitic, palmitoleic and arachidonic acids, and with the proviso that, when the estrogen is steroidal and has a steroid ring system with a C-3 position and a hydroxyl group at the C-3 position, the acyl group of the fatty acid is attached to the hydroxyl group at the C-3 position of the steroid ring system to form the fatty acid monoester; in combination with amounts of at least one member selected from the group consisting of pharmaceutically acceptable excipients and cosmetically acceptable excipients in an amount sufficient for the purposes thereof.

* * * * *